(12) United States Patent
McAtee

(10) Patent No.: US 6,179,885 B1
(45) Date of Patent: Jan. 30, 2001

(54) AROMATIC MANNICH COMPOUND-CONTAINING COMPOSITION AND PROCESS FOR MAKING SAME

(75) Inventor: Rodney John McAtee, Kingston Upon Hill (GB)

(73) Assignee: The Lubrizol Corporation, Wickliffe, OH (US)

( * ) Notice: Under 35 U.S.C. 154(b), the term of this patent shall be extended for 0 days.

(21) Appl. No.: 09/337,997

(22) Filed: Jun. 22, 1999

(51) Int. Cl.$^7$ ................................ C10L 1/22; C08G 8/04
(52) U.S. Cl. ........................ 44/415; 528/129; 528/152; 528/162; 524/765; 524/767; 44/412; 44/417; 44/436; 44/450; 44/639
(58) Field of Search ...................... 528/129, 152, 528/162; 524/765, 767; 44/412, 415, 417, 436, 450, 639

(56) References Cited

U.S. PATENT DOCUMENTS

| | | |
|---|---|---|
| 3,658,494 | 4/1972 | Dorer, Jr. . |
| 3,658,495 | 4/1972 | Dorer, Jr. . |
| 3,948,619 | 4/1976 | Worrel . |
| 3,980,569 | 9/1976 | Pindar et al. . |
| 4,006,089 | 2/1977 | Chibnik . |
| 4,231,759 | 11/1980 | Udelhofen et al. . |
| 4,708,809 | 11/1987 | Davis . |
| 4,973,789 | 11/1990 | Karn et al. . |
| 5,300,701 | 4/1994 | Cherpeck . |
| 5,663,457 | 9/1997 | Kolp . |
| 5,873,917 * | 2/1999 | Daly ........................................ 44/443 |
| 5,876,468 | 3/1999 | Moreton . |

FOREIGN PATENT DOCUMENTS 0831141   3/1996  (EP) .

* cited by examiner

Primary Examiner—Samuel A. Acquah
(74) Attorney, Agent, or Firm—Michael F. Esposito; Samuel B. Laferty

(57) ABSTRACT

This invention relates to a composition, comprising:
(I) an aromatic Mannich compound derived from:
(A) a hydroxy containing aromatic compound having the formula

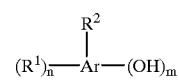
(A-1)

wherein in Formula (A-1): Ar is an aromatic group; m is 1, 2 or 3; n is a number from 1 to about 4; with the proviso that the sum of m and n does not exceed the number of available positions on Ar that can be substituted; each $R^1$ independently is a hydrocarbyl group of up to about 400 carbon atoms; and $R^2$ is H, amino or carboxyl;
(B) an aldehyde or ketone having the formula

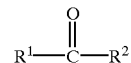
(B-1)

or a precursor thereof; wherein in Formula (B-1): $R^1$ and $R^2$ independently are H or hydrocarbyl groups having from 1 to about 18 carbon atoms; and $R^2$ can also be a carbonyl-containing hydrocarbyl group having from 1 to about 18 carbon atoms; and
(C) a mixture of water and an amine, said amine containing at least one primary or secondary amino group; and
(II) alcohol.

The invention also relates to a process for making the foregoing composition.

34 Claims, No Drawings

AROMATIC MANNICH COMPOUND-CONTAINING COMPOSITION AND PROCESS FOR MAKING SAME

TECHNICAL FIELD

The invention relates to aromatic Mannich compound-containing compositions and to a process for making these compounds. The aromatic Mannich compounds are dispersed in alcohol, and are useful as detergent additives for hydrocarbon fuels.

BACKGROUND OF THE INVENTION

Hydrocarbon fuels generally contain numerous deposit-forming substances. When used in internal combustion engines, deposits tend to form on and around constricted areas of the engine in contact with the fuels. In diesel engines, deposits tend to accumulate in the fuel injection system, thereby hampering good performance of the engine. In spark ignition engines deposits can build up on engine intake valves leading to progressive restriction of gaseous fuel mixture flow into the combustion chamber and also to valve sticking. It is common practice therefore to incorporate a detergent in the fuel composition for the purpose of inhibiting the formation, and facilitating the removal, of engine deposits, thereby improving engine performance. Mannich condensation products, obtained by reacting hydrocarbon-substituted phenols with aldehydes and amines, are known as detergents for fuels.

SUMMARY OF THE INVENTION

This invention relates to a composition, comprising (I) an aromatic Mannich compound derived from:
(A) a hydroxy containing aromatic compound having the formula

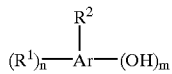
(A-1)

wherein in Formula (A-1): Ar is an aromatic group; m is 1, 2 or 3; n is a number from 1 to about 4; with the proviso that the sum of m and n does not exceed the number of available positions on Ar that can be substituted; each $R^1$ independently is a hydrocarbyl group of up to about 400 carbon atoms; and $R^2$ is H, amino or carboxyl;

(B) an aldehyde or ketone having the formula

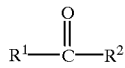
(B-1)

or a precursor thereof; wherein in Formula (B-1): $R^1$ and $R^2$ independently are H or hydrocarbyl groups having from 1 to about 18 carbon atoms; and $R^2$ can also be a carbonyl-containing hydrocarbyl group having from 1 to about 18 carbon atoms; and (C) a mixture of water and an amine, said amine containing at least one primary or secondary amino group; and (II) alcohol.

This invention also relates to a process, comprising:

reacting (A) a hydroxy containing aromatic compound having the formula

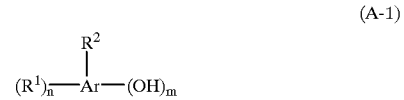

wherein in Formula (A-1): Ar is an aromatic group; m is 1, 2 or 3; n is a number from 1 to about 4; with the proviso that the sum of m and n does not exceed the number of available positions on Ar that can be substituted; each $R^1$ independently is H or a hydrocarbyl group having from 1 to about 400 carbon atoms; and $R^2$ is H, amino or carboxyl;

with (B) an aldehyde or ketone having the formula

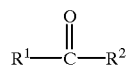
(B-1)

or a precursor thereof; wherein in Formula (B-1): $R^1$ and $R^2$ independently are H or hydrocarbyl groups having from 1 to about 18 carbon atoms; and $R^2$ can also be a carbonyl-containing hydrocarbyl group having from 1 to about 18 carbon atoms; and (C) a mixture of water and an amine, said amine containing at least one primary or secondary amino group;

in the presence of alcohol.

These aromatic Mannich compound-containing compositions are characterized by relatively high nitrogen levels which provide for enhanced detergent properties when used in fuels.

DETAILED DESCRIPTION OF THE PREFERRED EMBODIMENTS

As used herein, the term "hydrocarbyl substituent," "hydrocarbyl group" or "hydrocarbon group" is used to refer to a group having one or more carbon atoms directly attached to the remainder of a molecule and having a hydrocarbon or predominantly hydrocarbon character. Examples include:

(1) purely hydrocarbon groups, that is, aliphatic (e.g., alkyl, alkenyl or alkylene), and alicyclic (e.g., cycloalkyl, cycloalkenyl) groups, aromatic groups, and aromatic-, aliphatic-, and alicyclic-substituted aromatic groups, as well as cyclic groups wherein the ring is completed through another portion of the molecule (e.g., two substituents together forming an alicyclic group);

(2) substituted hydrocarbon groups, that is, hydrocarbon groups containing non-hydrocarbon groups which, in the context of this invention, do not alter the predominantly hydrocarbon nature of the group (e.g., halo, hydroxy, alkoxy, mercapto, alkylmercapto, nitro, nitroso, and sulfoxy);

(3) hetero substituted hydrocarbon groups, that is, hydrocarbon groups containing substituents which, while having a predominantly hydrocarbon character, in the context of this invention, contain other than carbon in a ring or chain otherwise composed of carbon atoms. Heteroatoms include sulfur, oxygen, nitrogen. In general, no more than two, and in one embodiment no more than one, non-hydrocarbon substituent is present for every ten carbon atoms in the hydrocarbon group.

The term "lower" when used in conjunction with terms such as alkyl, alkenyl, and alkoxy, is intended to describe such groups that contain a total of up to 7 carbon atoms.

The term "fuel-soluble" refers to materials that are soluble in a normally liquid hydrocarbon fuel (e.g. gasoline or diesel fuel) to the extent of at least one gram per 100 milliliters of fuels at 25° C.

In Formula (A-1), Ar may be a benzene or a naphthalene nucleus. Ar may be a coupled aromatic compound, the coupling agent preferably being O, S, CH$_2$, a lower alkylene group having from 1 to about 6 carbon atoms, NH, and the like, with R$^1$ and OH generally being pendant from each aromatic nucleus. Examples of specific coupled aromatic compounds include diphenylamine, diphenylmethylene and the like. m is usually from 1 to 3, and in one embodiment 1 or 2, and in one embodiment 1. n is usually from 1 to 4, and in one embodiment 1 or 2, and in one embodiment 1. R$^2$ may be H, amino or carboxyl, and in one embodiment R$^2$ is H. R$^1$ is a hydrocarbyl group of up to about 400 carbon atoms, and in one embodiment up to about 250 carbon atoms, and in one embodiment up to about 150 carbon atoms. R$^1$ can be an alkyl group, alkenyl group or cycloalkyl group.

In one embodiment, R$^1$ is a hydrocarbyl group derived from an olefin polymer. The olefin polymer may be derived from an olefin monomer of 2 to about 10 carbon atoms, and in one embodiment about 3 to about 6 carbon atoms, and in one embodiment about 4 carbon atoms. Examples of the monomers include ethylene; propylene; butene-1; butene-2; isobutene; pentene-1; heptene-1; octene-1; nonene-1; decene-1; pentene-2; or a mixture of two or more thereof.

In one embodiment, R$^1$ is a polyisobutene group. The polyisobutene group may be made by the polymerization of a C$_4$ refinery stream having a butene content of about 35 to about 75% by weight and an isobutene content of about 30 to about 60% by weight.

In one embodiment, R$^1$ is a polyisobutene group derived from a polyisobutene having a high methylvinylidene isomer content, that is, at least about 70% methylvinylidene. Suitable high methylvinylidene polyisobutenes include those prepared using boron trifluoride catalysts. The preparation of such polyisobutenes in which the methylvinylidene isomer comprises a high percentage of the total olefin composition is described in U.S. Pat. Nos. 4,152,499 and 4,605,808, the disclosures of each of which are incorporated herein by reference.

Examples of suitable polyisobutenes having a high methylvinylidene content include Ultravis 10, a polyisobutene having a number average molecular weight of about 950 and a methylvinyidiene content of about 82%, and Ultravis 30, a polyisobutene having a number average molecular weight of about 1300 and a methylvinylidene content of about 74%, both available from BP Amoco.

The polyisobutene contemplated for use in the present invention may have a number average molecular weight in the range of about 200 to 5,000, and in one embodiment in the range of about 250 to 3,000, and in one embodiment the range of about 300 to 2,500, and in one embodiment in the range of about 500 to about 2300, and in one embodiment about 750 to about 1500.

In a preferred embodiment, component (A) is a polyisobutene-substituted phenol wherein the polyisobutene substituent is derived from a polyisobutene having a number average molecular weight in the range of about 300 to about 5000, and in one embodiment about 500 to about 2500, and a methylvinylidene isomer content of at least about 70%, and in one embodiment at least about 80%.

In Formula (B-1), R$^1$ and R$^2$ may be independently H, hydrocarbyl groups containing 1 to about 18 carbon atoms, and in one embodiment 1 to about 6 carbon atoms, and in one embodiment 1 or 2 carbon atoms. In one embodiment, R$^1$ and R$^2$ may be independently phenyl or alkyl-substituted phenyl groups having up to about 18 carbon atoms, and in one embodiment up to about 12 carbon atoms. R$^2$ can also be a carbonyl-containing hydrocarbyl group of 1 to about 18 carbon atoms, and in one embodiment 1 to about 6 carbon atoms. Examples of suitable aldehydes and ketones (B) include formaldehyde, acetaldehyde, propionaldehyde, butyraldehyde, valeraldehyde, benzaldehyde, and the like, as well as acetone, methyl ethyl ketone, ethyl propyl ketone, butyl methyl ketone, glyoxal, glyoxylic acid, and the like. Precursors of such compounds which react as aldehydes under reaction conditions of the present invention can also be utilized and include paraformaldehyde, formalin, trioxane and the like. Paraformaldehyde and aqueous solutions of formalin (e.g., about 35% to about 45% by weight formalin in water) are preferred reactants. Mixtures of the various (B) reactants can be utilized.

The third reactant used in preparing the aromatic Mannich is (C) a mixture of water and an amine, the amine containing at least one primary or secondary amino group. The weight ratio of amine to water is typically about 50:50 to about 99:1, and in one in one embodiment about 70:30 to about 95:5, and in one embodiment about 85:15 to about 95:5, and in one embodiment about 90:10. The amine is characterized by the presence of at least one >N—H group. The remaining valences of the foregoing nitrogen atom may be satisfied by hydrogen, amino, or organic groups bonded to the nitrogen atom through direct carbon-to-nitrogen linkages.

The amine may be represented by the formula

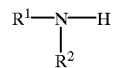

(C-1)

In Formula (C-1), R$^1$ and R$^2$ are independently hydrogen, hydrocarbyl groups, amino-substituted hydrocarbyl groups, hydroxy-substituted hydrocarbyl groups, or alkoxy-substituted hydrocarbyl groups. Thus, the amine may be ammonia, aliphatic amines, aliphatic hydroxy or thioamines, aromatic amines, heterocyclic amines, or carboxylic amines. The amines may be primary or secondary amines and may also be polyamines such as alkylene amines, arylene amines, cyclic polyamines, and the hydroxy-substituted derivatives of such polyamines. Examples include methylamine, dimethylamine, N-methyl-ethylamine, N-methyl-octylamine, N-cyclohexyl-amine, dibutylamine, cyclohexylamine, aniline, dodecylamine, octadecylamine, o-phenylenediamine, N,N'-di-n-butyl-p-phenylenediamine, morpholine, piperazine, tetrahydropyrazine, indole, hexahydro-1,3,5-triazine, 1-H-1,2,4-triazole, melamine, bis-(p-aminophenyl)methane, phenyl-methylenimine, menthanediamine, cyclohexylamine, pyrrolidine, 3-amino-5, 6-diphenyl-1,2,4-triazine, ethanolamine, diethanolamine, quinonediimine, 1,3-indandiimine, 2-octadecylimidazoline, 2-phenyl-4-methyl-imidazolidine, oxazolidine, 2-heptyl-oxazolidine, and mixtures of two or more thereof.

The amine may be a hydroxyl-containing amine represented by the formula

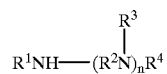

(C-2)

In Formula (C-2), each of R$^1$, R$^3$ and R$^4$ is independently H or a hydrocarbyl, hydroxyhydrocarbyl, aminohydrocarbyl, or hydroxyaminohydrocarbyl group provided that at least one of $R^3$ is a hydroxyhydrocarbyl or a hydroxyaminohydrocarbyl group. $R^2$ is preferably an alkylene group, more preferably ethylene or propylene, more preferably ethylene. n is a number ranging from zero to about 5. Examples include ethanolamine, 2-amino-1-butanol, 2-amino-2-methyl1-propanol, di-(3-hydroxypropyl)amine, 3-hydroxybutyl-amine, 4-hydroxybutylamine, 2-amino-1-butanol, 2-amino-2-methyl-1-propanol, 2-amino-1-propanol, 3-amino-2-methyl-1-propanol, 3-amino-1-propanol, 2-amino-2-methyl-1,3-propanediol, 2-amino-2-ethyl-1,3-propanediol, diethanolamine, di-(2-hydroxypropyl)-amine, N-(hydroxypropyl)-propylamine, N-(2-hydroxyethyl)-cyclohexylamine, 3-hydroxycyclopentylamine, N-hydroxyethyl piperazine, or a mixture of two or more thereof.

The amine may be a polyamine represented by the formula

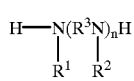 (C-3)

Formula (C-3), n is a number in the range of zero to about 10, more preferably about 1 to about 7. $R^1$ and $R^2$ are independently H or hydrocarbyl groups of up to about 30 carbon atoms. $R^3$ is an alkylene group that contains up to about 10 carbon atoms, with methylene, ethylene and propylene being preferred. These alkylene amines include methylene amines, ethylene amines, butylene amines, propylene amines, pentylene amines, hexylene amines, heptylene amines, octylene amines, other polymethylene amines, and also the cyclic and the higher homologues of such amines such as piperazines and amino-alkyl-substituted piperazines. Examples includes: ethylene diamine, triethylene tetramine, propylene diamine, decamethylene diamine, octamethylene diamine, di(heptamethylene)triamine, tripropylene tetramine, tetraethylene pentamine, trimethylene diamine, pentaethylene hexamine, di(trimethylene)-triamine, 2-heptyl-3-(2-aminopropyl)imidazoline, 4-methyl-imidazoline, 1,3-bis(2-amino-ethyl)imidazoline, pyrimidine, 1-(2-aminopropyl)piperazine. 1,4-bis(2-amino-ethyl)piperazine, and 2-methyl-1-(2-aminobutyl)piperazine, or a mixture of two or more thereof. Higher homologues such as are obtained by condensing two or more of the above-illustrated alkylene amines likewise are useful. Ethylene diamine is a preferred amine.

Hydroxyalkyl-substituted alkylene amines, i.e., alkylene amines having one or more hydroxyalkyl substituents on the nitrogen atoms, likewise are contemplated for use as the amine reactant. The hydroxyalkyl-substituted alkylene amines include those in which the alkyl group is a lower alkyl group. Examples of such amines include N-(2-hydroxyethyl)ethylene diamine, N,N'-bis(2-hydroxyethyl) ethylene diamine, 1-(2-hydroxyethyl)piperazine, monohydroxypropyl-substituted diethylene triamine, 1,4-bis-(2-hydroxypropyl)piperazine, di-hydroxypropyl-substituted tetraethylene pentamine, N-(3-hydroxypropyl) tetramethylene diamine, 2-heptadecyl-1(2-hydroxyethyl) imidazoline, and mixtures of two ore more thereof.

Higher homologues such as are obtained by condensation of the above-illustrated alkylene amines or hydroxyalkyl-substituted alkylene amines through amino groups or through hydroxy groups are likewise useful as the amine reactant. It will be appreciated that condensation through amino groups results in a higher amine accompanied with removal of ammonia and that condensation through the hydroxy groups results in products containing ether linkages accompanied with removal of water.

The ratio of equivalents of (A):(B):(C) is typically about 1:(1 to 2):(0.5 to 2). In one embodiment the ratio is about 1:1:1.

The preparation of the aromatic Mannichs may be carried out by adding the (A) hydroxyl containing aromatic compound, the (B) aldehyde or ketone, and (C) mixture of water and amine compound to a suitable vessel and heating to carry out the reaction. Reaction temperatures from about ambient to about the decomposition temperature of any component or the Mannich product can be utilized. The reaction is typically carried out at a temperature of about 40 to about 200° C., and in one embodiment about 80 to about 140° C. During reaction, water is drawn off as by sparging. The reaction is carried out in the presence of an alcohol.

The alcohol can be any fuel soluble hydrocarbon-based alcohol. These alcohols typically contain up to about 20 aliphatic carbon atoms, and in one embodiment 1 to about 20 carbon atoms, and in one embodiment 1 to about 10 carbon atoms. Examples include: methanol; ethanol; n-propanol; isopropanol; n-butanol; isobutanol; sec-butanol; tertbutanol; 3-methyl-1-butanol; n-pentanol; isopentanol; amyl alcohol; iso-amyl alcohol; cyclopentanol; n-hexanol; cyclohexanol; 2-methyl-4-pentanol; heptanol; octanol; 2-ethyl hexanol; decanol; dodecanol; tetradecanol; hexdecanol; octandecanol; allyl alcohol; crotyl alcohol; methyl vinyl carbinol; or a mixture of two or more thereof. A preferred alcohol is 2-ethyl hexanol. The weight ratio of the aromatic Mannich compound formed by the reaction of components (A), (B) and (C) to the alcohol may be from about 85:15 to about 10:90, and in one embodiment about 70:30 to about 50:50, and in one embodiment about 65:35.

The fuel compositions of the present invention contain a major proportion of a normally liquid fuel, usually a hydrocarbonaceous petroleum distillate fuel such as motor gasoline as defined by ASTM Specification D439 or diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain an amount of the aromatic Mannich compound-containing composition of this invention sufficient to provide it with enhanced detergent properties; usually this amount is about 10 to about 1000 parts by weight of the aromatic Mannich compound-containing composition of this invention per million parts of fuel. When the fuel is gasoline, the aromatic Mannich compound-containing composition may be present at a concentration of about 20 to about 1000 ppm. When the fuel is diesel fuel, the aromatic Mannich compound-containing composition may be present at a concentration of about 10 to about 500 ppm.

The fuel composition may contain, in addition to the aromatic Mannich compound-containing composition of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-di-tertiary-butyl-4-methylphenol, rust inhibitors such as alkylated succinic acids and anhydrides, bacteriostatic agents, gum inhibitors, metal deactivators, demulsifiers, upper cylinder lubricants and anti-icing agents. These additives may also include other ashless dispersants or detergents in addition to the foregoing aromatic Mannich compounds such as hydrocarbyl-succinimides, hydrocarbyl-amines, borated compounds, polether amines, and the like.

EXAMPLE

Part A:

Phenol (203.2 g, 2.16 mol) is melted at 40° C. and added to boron trifluoride etherate (73.5 ml, 0.60 mol) in a 5 liter round bottomed flask. Ultravis 10 (1040 g, 1.09 mol), is dissolved in hexane (1863 ml) and the solution is added to the flask containing the phenol via a pressure equalizing dropping funnel, at a rate sufficient to maintain the temperature of the reaction mixture at 22–27° C. over a period of three hours. The solution is stirred for an additional 16 hours at room temperature before ammonia (400 ml of 30% w/w aqeous, 2.88 mol) is added. Water (1000 ml) is added and the mixture is stirred. The solution is separated into an organic layer and an aqueous layer using a five liter separating funnel. The aqueous layer is extracted using hexane. Four extration steps are used, with 500 ml of hexane being used in each extraction step. The organic layers from the four extraction steps are combined and dried over $MgSO_4$ overnight, then filtered through a 12 mm Celite pad. The solvent is removed from the filtrate at 80° C./23"Hg on a rotary evaporator. The product is polyisobutene-substituted phenol with a para to ortho ratio of about 3:1.

Part B:

The polyisobutene-substituted phenol from Part A (300 g, 0.295 mol), paraformaldehyde (10.17 g, 0.339 mol) and 2-ethyl hexanol (177.56 g) are charged to a round-bottomed flask and heated to 100° C. A mixture of water and ethylene diamine (1.95 g of water, 19.50 g of ethylene diamine) is then added over a period of 20 minutes via a pressure equalizing dropping funnel. The reaction mixture is heated to 115° C. for 0.5 hour and 7.26 ml of water are collected. The reaction mixture is then refluxed at 130° C. for 3 hours. The product is comprised of an aromatic Mannich compound (329.67 g) dissolved the 2-ethyl hexanol (177.56 g). The product has a nitrogen content of 1.60% and an alkalinity value of 62 mg KOH $g^{-1}$.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A composition, comprising (I) an aromatic Mannich compound derived from:
(A) a hydroxy containing aromatic compound having the formula

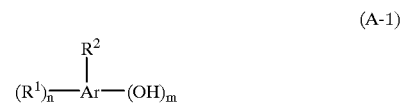

wherein in Formula (A-1): Ar is an aromatic group; m is 1, 2 or 3; n is a number from 1 to about 4; with the proviso that the sum of m and n does not exceed the number of available positions on Ar that can be substituted; each $R^1$ independently is a hydrocarbyl group of up to about 400 carbon atoms; and $R^2$ is H, amino or carboxyl;

(B) an aldehyde or ketone having the formula

or a precursor thereof; wherein in Formula (B-1): $R^1$ and $R^2$ independently are H or hydrocarbyl groups having from 1 to about 18 carbon atoms; and $R^2$ can also be a carbonyl-containing hydrocarbyl group having from 1 to about 18 carbon atoms; and (C) a mixture of water and an amine, said amine containing at least one primary or secondary amino group; and (II) alcohol.

2. The composition of claim 1 wherein in Formula (A-1), Ar is a benzene nucleus, $R^2$ is H, n is 1, and m is 1.

3. The composition of claim 1 wherein in Formula (A-1), $R^1$ is an alkyl, alkenyl or cycloalkyl group.

4. The composition of claim 1 wherein in Formula (A-1), $R^1$ is a hydrocarbyl group derived from an olefin polymer.

5. The composition of claim 1 wherein in Formula (A-1), $R^1$ is a polyolefin group, said polyolefin group being derived from ethylene; propylene, butene-1; butene-2; isobutene; pentene-1; hexene-1; heptene-1; octene-1; nonene-1; decene-1; pentene-2; or a mixture of two or more thereof.

6. The composition of claim 1 wherein in Formula (A-1), $R^1$ is a polyisobutene group.

7. The composition of claim 1 wherein in Formula (A-1), $R^1$ is a polyisobutene group made by the polymerization of a $C_4$ refinery stream having a butene content of about 35 to about 75% by weight and an isobutene content of about 30 to about 60% by weight.

8. The composition of claim 1 wherein in Formula (A-1), $R^1$ is derived from a polyisobutene having a methylvinylidene isomer content of at least about 70%.

9. The composition of claim 1 wherein in Formula (A-1), $R^1$ is a polyisobutene group having a number average molecular weight of about 300 to about 5000.

10. The composition of claim 1 wherein in Formula (B-1), $R^1$ and $R^2$ are independently H or hydrocarbyl groups of 1 to about 6 carbon atoms.

11. The composition of claim 1 wherein (B) is formaldehyde, acetaldehyde, propionaldehyde, butyraldehyde, valeraldehyde, benzaldehyde, acetone, methyl ethyl ketone, ethyl propyl ketone, butyl methyl ketone, glyoxal or glyoxylic acid.

12. The composition of claim 1 wherein said pecursor of said aldehyde or ketone is paraformaldeyde, formalin or trioxane.

13. The composition of claim 1 wherein (B) is paraformaldehyde.

14. The composition of claim 1 wherein said amine is a compound represented by the formula

wherein in Formula (C-1), $R^1$ and $R^2$ are independently hydrogen, hydrocarbyl groups, amino-substituted hydrocarbyl groups, hydroxy-substituted hydrocarbyl groups, or alkoxy-substituted hydrocarbyl groups.

15. The composition of claim 1 wherein said amine is ammonia; methylamine; dimethylamine; N-methyl-ethylamine; N-methyloctylamine; N-cyclohexyl-amine; dibutylamine; cyclohexylamine; aniline; dodecylamine; octadecylamine; o-phenylene-diamine; N,N'-di-n-butyl-p-phenylenediamine; morpholine; piperazine; tetrahydropyrazine; indole; hexahydro-1,3,5-triazine; 1-H-1,2,4-triazole; melamine; bis-(p-aminophenyl)methane; phenyl-methylenimine; menthanediamine; cyclohexylamine; pyrrolidine; 3-amino-5,6-diphenyl-1,2,4-triazine; ethanolamine; diethanolamine; quinonediimine; 1,3-indandiimine; 2-octadecylimidazoline; 2-phenyl-4-methylimidazoline; oxazolidine; 2-heptyl-oxazolidine; or a mixture of two or more thereof.

16. The composition of claim 1 wherein said amine is a hydroxyl-containing amine represented by the formula

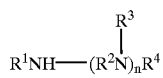

wherein in Formula (C-2): each of $R^1$, $R^3$ and $R^4$ independently is H or a hydrocarbyl, hydroxyhydrocarbyl, aminohydrocarbyl, or hydroxyaminohydrocarbyl group provided that at least one of $R^3$ is a hydroxyhydrocarbyl or a hydroxy-aminohydrocarbyl group; $R^2$ is an alkylene group; and n is a number in the range of zero to about 5.

17. The composition of claim 1 wherein said amine is ethanolamine; 2-amino-1-butanol; 2-amino-2-methyl-1-propanol; di-(3-hydroxypropyl)amine; 3-hydroxybutyl-amine; 4-hydroxybutyl-amine; 2-amino-1-butanol; 2-amino-2-methyl-1-propanol; 2-amino-1-propanol; 3-amino-2-methyl-1-propanol; 3-amino-1-propanol; 2-amino-2-methyl-1,3-propanediol; 2-amino-2-ethyl-1,3-propanediol; diethanolamine; di-(2-hydroxypropyl)amine; N-(hydroxypropyl)-propylamine; N-(2-hydroxyethyl)-cyclohexylamine; 3-hydroxycyclopentylamine; N-hydroxyethyl piperazine; or a mixture of two or more thereof.

18. The composition of claim 1 wherein said amine is a polyamine represented by the formula

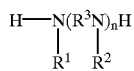

wherein in Formula (C-3): n is a number in the range of 1 to about 10; $R^1$ and $R^2$ are independently H or hydrocarbyl groups of 1 to about 30 carbon atoms; and $R^3$ is an alkylene group of 1 to about 10 carbon atoms.

19. The composition of claim 1 wherein said amine is ethylene diamine; triethylene tetramine; propylene diamine; decamethylene diamine; octamethylene diamine; di(heptamethylene)triamine; tripropylene tetramine; tetra-ethylene pentamine; trimethylene diamine; pentaethylene hexamine; di(trimethylene)-triamine; 2-heptyl-3-(2-aminopropyl)imidazoline; 4-methyl-imidazoline; 1,3-bis(2-aminoethyl)imidazoline; pyrimidine; 1-(2-aminopropyl) piperazine; 1,4-bis(2-aminoethyl)piperazine; 2-methyl-1-(2-amino-butyl)piperzine; or a mixture of two or more thereof.

20. The composition of claim 1 wherein said amine is ethylene diamine.

21. The composition of claim 1 wherein said alcohol is a fuel soluble hydrocarbon-based alcohol containing up to about 20 aliphatic carbon atoms.

22. The composition of claim 1 wherein said alcohol is methanol; ethanol; n-propanol; isopropanol; n-butanol; isobutanol; sec-butanol; tert-butanol; 3-methyl-1-butanol; n-pentanol; isopentanol; amyl alcohol; iso-amyl alcohol; cyclopentanol; n-hexanol; cyclohexanol; 2-methyl-4-pentanol; heptanol; octanol; 2-ethyl hexanol; decanol; dodecanol; tetradecanol; hexdecanol; octadecanol; allyl alcohol; crotyl alcohol; methyl vinyl carbinol; or a mixture of two or more thereof.

23. The composition of claim 1 wherein said alcohol is 2-ethyl hexanol.

24. The composition of claim 1 wherein the equivalent ratio of (A):(B):(C) is about 1:(1 to 2):(0.5 to 2).

25. The composition of claim 1 wherein the weight ratio of said amine to said water is from about 50:50 to about 99:1.

26. The composition of claim 1 wherein the weight ratio of said aromatic Mannich compound (I) to said alcohol (II) is from about 85:15 to about 10:90.

27. A composition, comprising:
(I) an aromatic Mannich compound derived from: (A) a polyiso-butene-substituted phenol wherein the polyisobutene substituent is derived from a polyisobutene having a methylvinylidene isomer content of at least about 70%; (B) paraformaldehyde; and (C) a mixture of water and ethylene diamine; and
(II) 2-ethyl hexanol.

28. A fuel composition comprising a major amount of a normally liquid hydrocarbon fuel, and a minor amount of the composition of claim 1.

29. A process, comprising:
reacting (A) a hydroxy containing aromatic compound having the formula

wherein in Formula (A-1): Ar is an aromatic group; m is 1, 2 or 3; n is a number from 1 to about 4; with the proviso that the sum of m and n does not exceed the number of available positions on Ar that can be substituted; each $R^1$ independently is H or a hydrocarbyl group having from 1 to about 400 carbon atoms; and $R^2$ is H, amino or carboxyl;

with (B) an aldehyde or ketone having the formula

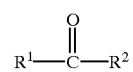

or a precursor thereof; wherein in Formula (B-1): $R^1$ and $R^2$ independently are H or hydrocarbyl groups having from 1 to about 18 carbon atoms; and $R^2$ can also be a carbonyl-containing hydrocarbyl group having from 1 to about 1 8 carbon atoms; and and (C) a mixture of water and an amine, said amine containing at least one primary or secondary amino group;

in the presence of alcohol.

30. The process of claim 29 wherein the equivalent ratio of (A):(B):(C) is about 1:(1 to 2):(0.5 to 2).

31. The process of claim 29 wherein the weight ratio of said amine to said water is from about 50:50 to about 99:1.

32. The process of claim 29 wherein the weight ratio of the reaction product of (A), (B) and (C) to said alcohol is from about 85:15 to about 10:90.

33. The process is of claim 29 wherein said process is conducted at a temperature of about 40 to about 200° C.

34. A process for making an aromatic Mannich compound, comprising:

reacting (A) a polyisobutene-substituted phenol wherein the polyisobutene substituent is derived from a polyisobutene having a methylvinylidene isomer content of at least about 70%; with (B) paraformaldehyde; and (C) a mixture of water and ethylene diamine;

in the presence of 2-ethyl hexanol.

* * * * *